(12) United States Patent
Baloch et al.

(10) Patent No.: US 9,830,427 B2
(45) Date of Patent: Nov. 28, 2017

(54) METHOD FOR INTRACRANIAL ANEURYSM ANALYSIS AND ENDOVASCULAR INTERVENTION PLANNING

(75) Inventors: Sajjad Hussain Baloch, Monmouth Junction, NJ (US); Sandra Sudarsky, Bedminster, NJ (US); Ying Zhu, Monmouth Junction, NJ (US); Ashraf Mohamed, Tokyo (JP); Komal Dutta, Hoffman Estates, IL (US); Durga Namburu, Bartlett, IL (US); Puthenveettil Nias, Algonquin, IL (US); Gary S. Martucci, Algonquin, IL (US); Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 43 days.

(21) Appl. No.: 13/526,719

(22) Filed: Jun. 19, 2012

(65) Prior Publication Data

US 2012/0323547 A1 Dec. 20, 2012

Related U.S. Application Data

(60) Provisional application No. 61/498,822, filed on Jun. 20, 2011.

(51) Int. Cl.
*G06F 19/00* (2011.01)
(52) U.S. Cl.
CPC ................... *G06F 19/3437* (2013.01)
(58) Field of Classification Search
CPC ................................. A61F 2002/823
See application file for complete search history.

(56) References Cited

U.S. PATENT DOCUMENTS

2006/0184066 A1* 8/2006 Karmonik ............ A61B 5/103
600/587

OTHER PUBLICATIONS

Appanaboyina et al. "Simulation of intracranial aneurysm stenting: Techniques and challenges," (Comput. Methods, vol. 198 (2009) pp. 3567-3582).*
Piccinelli et al. "A Framework for Geometric Analysis of Vascular Structures: Application to Cerebral Aneurysms" (IEEE Transactions of Medical Imagine, vol. 28 (2009) pp. 1141-1155).*
Chan, H. M., et al. "2D-3D vascular registration between digital subtraction angiographic (DSA) and magnetic resonance angiographic (MRA) images." Biomedical Imaging: Nano to Macro, 2004. IEEE International Symposium on. IEEE, 2004.*
Hernandez et al. "Non-parametric geodesic active regions: Method and evaluation for cerebral aneurysms segmentation in 3DRA and CTA," (Medical Image Analysis, vol. 11 (2007) pp. 224-241).*
Sang et al. "Knowledge-based adaptive thresholding segmentation of digital subtraction angiography images"(Image and Vision Computing, vol. 25 (2007)).*
Sugahara et al. "Comparison of 2D and 3D Digital Subtraction Angiography in Evaluation of Intracranial Aneurysms" (AJNR A, J. Neuroradiol, vol. 23 (2002) pp. 1545-1552).*
G.N. Foutrakis, H. Yonas, and R.I. Sclabassi, "Saccular Aneurysm Formation in Curved and Bifurcating Arteries", American Journal of Neuroradiology, 1999, pp. 1309-1317, vol. 20, No. 7.
B. Weir, "Unruptured intracranial aneurysms: a review", Journal of Neurosurgery, 2002, pp. 3-42, vol. 96, No. 1.
A. Mohamed, E. Sgouritsa, H. Morsi, H. Shaltoni, M. E. Mawad, and I. A. Kakadiaris, Computer-Aided Planning for Endovascular Treatment of Intracranial Aneurysms (CAPETA), Proceedings of SPIE Conference on Medical Imaging, 2010, pp. 762532-1 through 762532-9, vol. 7625.
S. Baloch, E. Cheng, Y. Zhu, A. Mohamed, H. Ling, and T. Fang,"Shape based conditional random fields for the segmentation of intracranial aneurysms", MeshMed workshop on Mesh Processing in Medical Image Analysis in conjunction with MICCAI, 2011, pp. 1-12.
R. Gasparotti, R. Liserre, Intracranial aneurysms, Eur Radiology, 2005, pp. 441-447, vol. 15.
E. Vivas, A. Marzo, R. Hose, and A.F. Frangi, "Three-dimensional morphological analysis of intracranial aneurysms: A fully automated method for aneurysm sac isolation and quantification", Medical Physics, 2011, pp. 2439-2449, vol. 38, No. 5.
Otsu, N., "A threshold selection method from gray-level histograms", IEEE Transactions on Systems, Man, and Cybernetics, 1979, pp. 62-66, vol. 9.

* cited by examiner

*Primary Examiner* — Anna Skibinsky

(57) ABSTRACT

A method (100) of aneurysm analysis (110) and virtual stent simulation (120) for endovascular treatment of sidewall intracranial aneurysms.

14 Claims, 12 Drawing Sheets

(a)

(b)

METHOD FOR INTRACRANIAL ANEURYSM ANALYSIS AND ENDOVASCULAR INTERVENTION PLANNING

CROSS-REFERENCE TO RELATED APPLICATIONS

This application claims the benefit of Provisional U.S. Patent Application Ser. No. 61/498,822 entitled, "System for Intracranial Aneurysms Analysis and Virtual Stent Planning", filed in the name of Sajjad Hussain Baloch, Sandra Sudarsky, Ying Zhu, Ashraf Mohamed, Thomas Redel, Komal Dutta, Durga Namburu, Puthenveettil Nias, and Gary Martucci, on Jun. 20, 2011.

FIELD OF THE INVENTION

The present invention generally relates to endovascular interventions. More particularly, the present invention relates to assessing intracranial, cerebral aneurysms and planning for endovascular treatment.

BACKGROUND OF THE INVENTION

An intracranial aneurysm is a major vascular disease in the brain, attributed to local weakening of a blood vessel wall. It manifests in the form of a bulging vessel (called a "saccular aneurysm") or a dilated vessel (called a "fusiform aneurysm"). FIG. 1 shows three, separate exemplary images of saccular sidewall aneurysms, which make up about ninety percent of all intracranial aneurysms. Intracranial aneurysms frequently occur near areas of high arterial curvature or bifurcations, as these regions usually experience more hemodynamic stress than other arterial areas (this is further described in an article by G. N. Foutrakis, H. Yonas, and R. I. Sclabassi entitled, "Saccular Aneurysm Formation in Curved and Bifurcating Arteries", American Journal of Neuroradiology, 1999, pg 1309-1317, vol. 20, no. 7). If left untreated, an aneurysm grows in size, thereby further weakening the vessel wall strength and increasing the risk of rupture. Rupture may lead to subarachnoid hemorrhage, neurological deficits, and, in up to 56% of cases, mortality (this is further described in an article by B. Weir entitled, "Unruptured intracranial aneurysms: a review", Journal of Neurosurgery, 2002, pp. 3-42, vol. 96, no. 1). In order to prevent an aneurysm's growth and reduce the risk of rupture, surgical intervention is typically required to reinforce the vessel wall and/or alter the blood flow pattern (via, for example, the placement of stents, wire coils, and other embolic material or devices), thereby reducing the pressure on vessel regions more prone to rupture.

Once diagnosed, aneurysms are carefully monitored and examined before making a surgical decision. To this end, the geometry of an aneurysm plays a crucial role. More specifically, studies have found a strong correlation between the risk of rupture of intracranial aneurysms and the morphological characteristics of aneurysms, such as volume, surface area, neck length, among others. Accurate quantification of these parameters is critical for appropriate endovascular treatment planning. Physicians and other medical professionals analyze various measurements of geometric primitives evaluated on an aneurysm, which allows them to carry out treatment and/or surgical planning. Currently, the measurements and the planning are done manually, which tend to be time-consuming and subjective. Further, the measurements and the planning activities may not always be organized in a well-coordinated manner. There is a need for a complete system and method that assists physicians, surgeons, and other medical professionals through diagnosis and treatment/surgical planning. Such systems and methods need to provide fast, accurate and reproducible morphological measurements and planning activities, such as, stent simulation and placement.

SUMMARY OF THE INVENTION

The aforementioned problems are obviated by the present invention which provides a computer-assisted method of aneurysm analysis and stent simulation, comprising: separating an aneurysm from the remainder of a parent blood vessel in an image of the parent blood vessel; creating shape models for the aneurysm and the parent blood vessel; extracting a plurality of characteristic features of the aneurysm from the shape model of the aneurysm; and simulating the placement of a stent in the parent blood vessel using the shape models for the aneurysm and the parent blood vessel and the plurality of characteristic features of the aneurysm. The method may also comprise conforming the shape of the stent to the shape of parent blood vessel.

The creating step may comprise creating a shape model of the remainder of the parent blood vessel without the aneurysm. The creating step may also comprise locating reference points on the image of the parent blood vessel to determine the extent of the parent blood vessel. In such case, the reference points may comprise a proximal point or plane on one side of the aneurysm, a distal point or plane on the other side of the aneurysm, and a dome point inside the aneurysm to provide relative positioning of the aneurysm with respect to the proximal and distal points or planes. The extracting step may comprise extracting a characteristic feature of the aneurysm which has been demonstrated to have a high correlation with the risk of aneurysm rupture. Also, the extracting step may comprise computing a plurality of measurements of the aneurysm. The computing step may comprise computing a plurality of measurements from the shape model of the separated aneurysm.

The present invention may also provide a computer-assisted method of analyzing an intracranial aneurysm and planning endovascular treatment for the aneurysm, comprising: performing vessel segmentation on an image that includes a parent blood vessel with an aneurysm; extracting the centerline of the parent blood vessel; separating the aneurysm from the parent blood vessel; reconstructing the parent blood vessel without the aneurysm; quantifying a plurality of characteristic features of the aneurysm; and deploying a virtual stent to fit the reconstructed parent blood vessel without the aneurysm. The image may comprise a 3D digital subtraction angiographic (DSA) image. The segmenting step may comprise reconstructing the surface representation of the blood vessel. The extracting step may comprise defining a segment or region of interest of the parent blood vessel. In such case, the defining step may comprise selecting proximal and distal points on the parent blood vessel around the aneurysm and one point in the aneurysm dome. In such case, the extracting step may also comprise generating a skeleton of the parent blood vessel without the aneurysm. The separating step may be implemented using the proximal and distal points on the parent blood vessel around the aneurysm and one point in the aneurysm dome.

The reconstructing step may comprise reconstructing the parent blood vessel without the aneurysm using the extracted centerline and computed diameters along the length of the parent blood vessel. In such case, the reconstructing step may also comprise reconstructing the extracted centerline without points projected thereon from the aneurysm. Further, the reconstructing the extracted centerline step may comprise reconstructing the extracted centerline from an interpolation of the points of the extracted centerline without points projected thereon from the aneurysm. The quantifying step may comprise computing the measurements of the plurality of characteristic features of the aneurysm. The measurements may comprise either two-dimensional or three-dimensional quantities or both. The deploying step may comprise designing and placing the virtual stent on the parent blood vessel. Also, the extracted centerline may define the axial stent deformation.

The present invention also provides a system for assessing the condition and planning the treatment of an intracranial aneurysm, comprising an imager that acquires image data of intracranial blood vessels and a processor that manipulates the acquired image data to separate an aneurysm from a parent blood vessel; reconstruct the parent blood vessel without the aneurysm; measure dimensions of the aneurysm and the reconstructed parent blood vessel; and simulate a stent to operably fit in the reconstructed parent blood vessel.

BRIEF DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
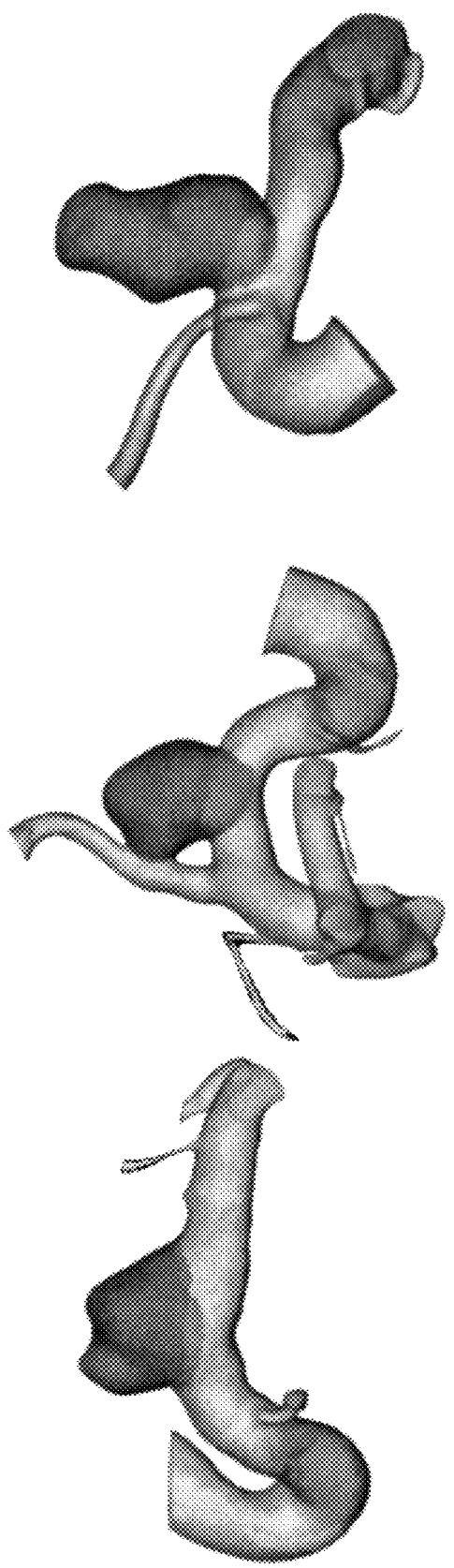
FIG. 1 shows exemplary images of intracranial sidewall aneurysms.
Figure 2:
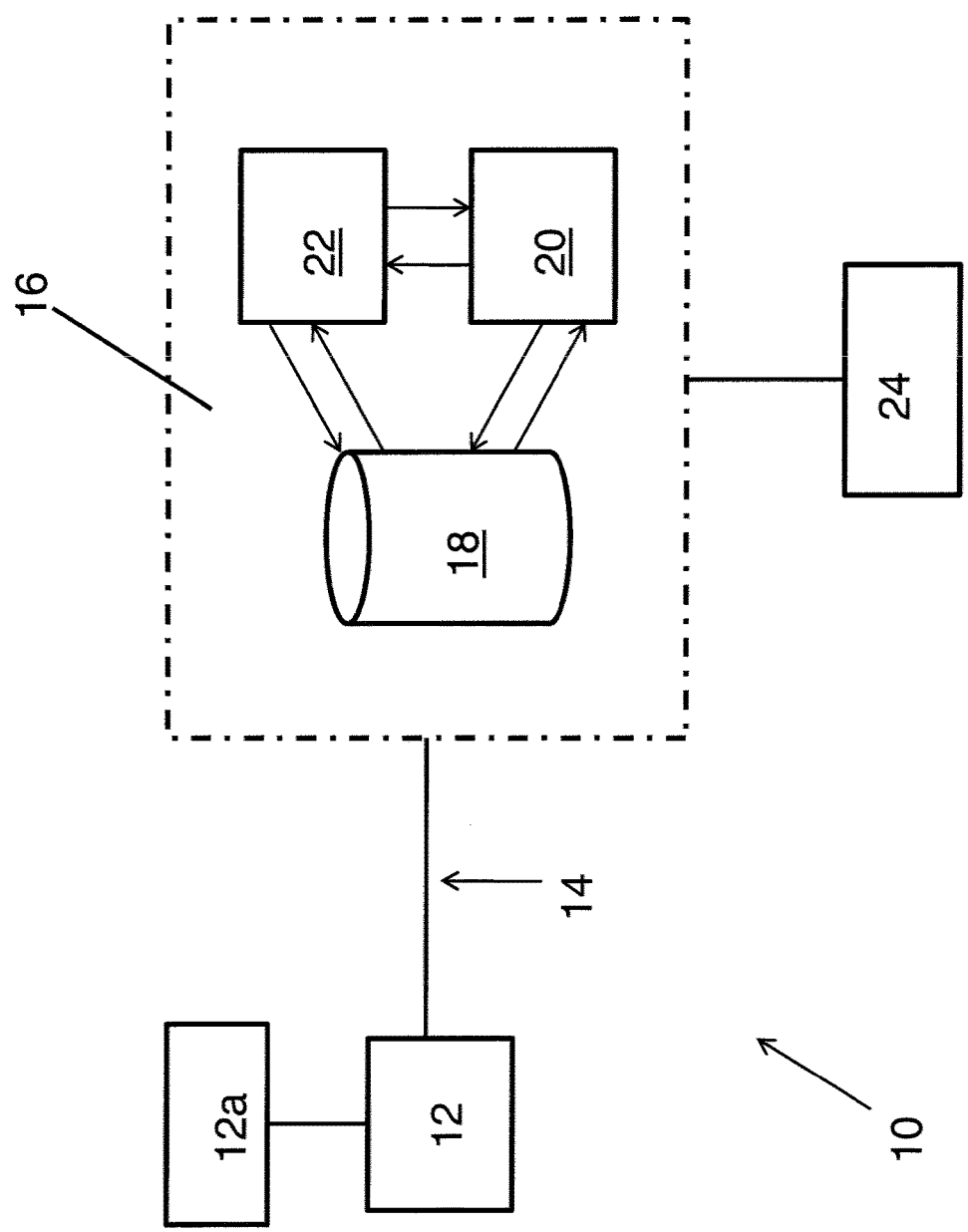
FIG. 2 is a block diagram of a medical imaging system (simplified) operable in accordance with the present invention.

FIG. 2 is a block diagram of a medical imaging system 10 (simplified) that operates in accordance with the present invention. The system 10 comprises a medical imaging scanner 12 that acquires image data of a patient under examination and, more particularly in this case, the vasculature in the brain of the patent. The scanner 12 may use any appropriate imaging modality to acquire the image data, for example, magnetic resonance, computed tomography, ultrasound, and X-ray imaging. The scanner 12 may acquire raw image data from multiple scanned views of the region of interest of the patient, reconstruct the images, and produce image data signals for the multiple views. The image data signals may be in Digital Imaging and Communications in Medicine (DICOM) format. Other formats may also be used.

The imaging scanner 12 is operably connected to a computer system 12a that controls the operation of the scanner 12 and, via a communication channel 14, to an image processing system 16 that processes the image data signals utilizing appropriate image processing software applications. The image processing system 16 has an image data archive or database 18, an application server 20, and a user workstation 22. The components of the image processing system 16 are interconnected via a communications network that may be implemented by physical connections, wireless communications, or a combination. The image data archive or database 18 is adapted to store the image data signals that are produced by the image scanner 12 as well as the results of any additional operations on the image data signals by the other components of the image processing system 16. The image data archive or database 18 may be a Picture Archiving and Communications System (PACS). Other types of image data archives or databases may also be used. The user workstation 22 is adapted to control the operation of the image processing system 16 and its various components. The user workstation 22 particularly operates the application server 20c and the various image processing software applications that are stored in, or are accessible by, the server 20. The application server 20 also manages and coordinates the image data sets among the image processing applications. The image processing applications may include, for example, visualization applications, computer-aided diagnosis (CAD) applications, medical image rendering applications, anatomical segmentation applications, or any other type of medical image processing application. The image processing applications may also include the methods of the present invention. The image data archive or database 18, applications server 20, and the user workstation may also each be connected to a remote computer network 24 for communication purposes or to access additional data or functionality. The workstation 22 may comprise appropriate user interfaces, like displays, storage media, input/output devices, etc.

The various components of the imaging system 10 are conventional and well known components. They may be configured and interconnected in various ways as necessary or as desired. The imaging system 10 and, in particular, the image processing system 16 is adapted to permit the imaging system 10 to operate and to implement methods in accordance with the present invention, for example, as shown in FIG. 3.

Figure 3:
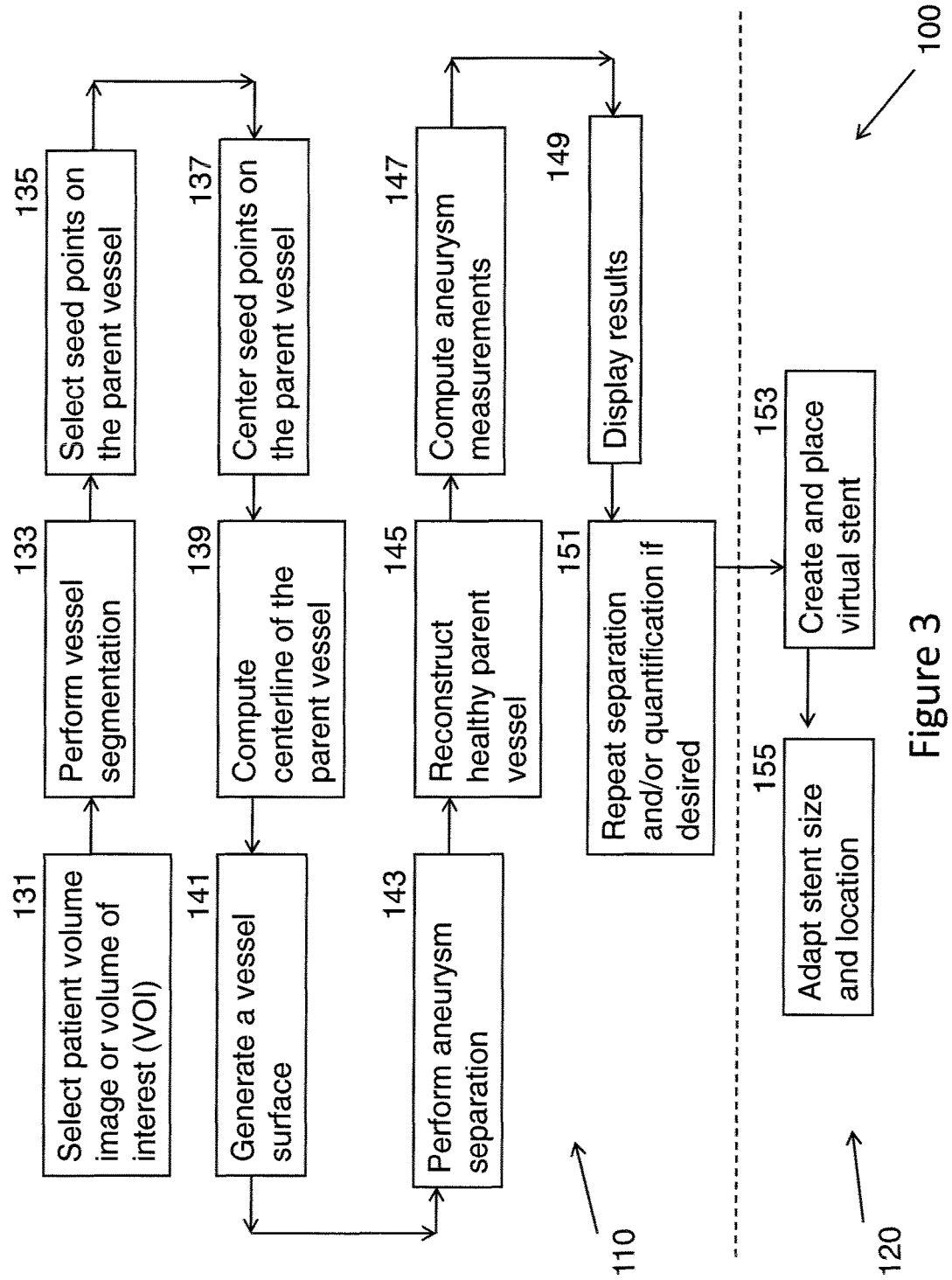
FIG. 3 is a flow chart of a method carried out in accordance with the present invention.

FIG. 3 shows a method 100 of processing image datasets of blood vessels carried out in accordance with the present invention. The method 100 is specifically directed to the analysis of intracranial aneurysms and the planning of endovascular treatment of intracranial aneurysms. The method 100 considers aspects of the recently proposed CAPETA framework (this is described in more detail in an article by A. Mohamed, E. Sgouritsa, H. Morsi, H. Shaltoni, M. E. Mawad, and I. A. Kakadiaris, Computer-Aided Planning for Endovascular Treatment of Intracranial Aneurysms (CAPETA), Proceedings of SPIE Conference on Medical Imaging, 2010, pp. 762532-1 through 762532-9, vol. 7625, which is incorporated by reference herein). In general, the method 100 allows a user to import patient data, and perform computer-assisted aneurysm analysis and stent simulation. As part of the aneurysm analysis, the aneurysm is separated from the parent vessel and a healthy parent vessel is reconstructed. Reconstruction then permits stent simulation.

The method 100 has two modes of operation as shown in the flow chart of FIG. 3. The first mode is an aneurysm analysis mode 110 that is used as an aid to diagnosis and provides a robust quantification of an aneurysm. The analysis mode 110 generally involves the separation of an aneurysm from the healthy part of the parent vessel, creation of aneurysm and vessel shape models, and computation of important aneurysm measurements, which have been demonstrated to have high correlation with the risk of aneurysm rupture, for example, neck angle. The shape of the aneurysm is analyzed by separating the aneurysm from the healthy vessel and the various aneurysm measurements are then computed from the separated aneurysm. These measurements play a crucial role in determining the condition of an aneurysm, and are presented to aid surgeons and physicians for diagnosis and planning/conducting treatment. The aneurysm separation forms a critical step, whose accuracy determines the eventual outcome in terms of surgical decisions, device selection, as well as patient recovery.

The second mode of operation is a stent simulation mode 120. In this mode 120, the measurements from the analysis mode 110 are used to simulate the placement of a virtual stent, and its geometry is made to conform to the shape of the parent vessel. For example, a healthy parent vessel is reconstructed following the aneurysm separation, which is subsequently used in the simulation mode 120 for the selection and placement of a virtual stent. The method 100 allows a user to adjust the automatic configuration of the stent.

Figure 4:
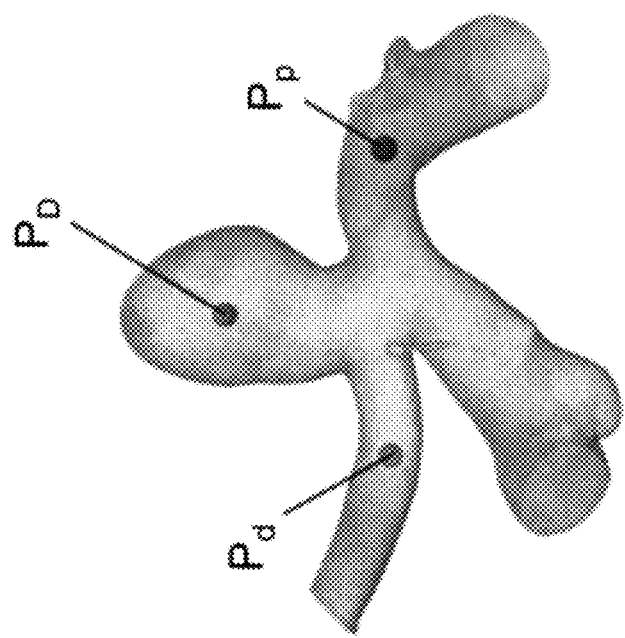
FIG. 4 is an image of a parent blood vessel with three seed points indicated.

As described in more detail below, there are two key components of the input to the method 100 that drive both the analysis and the simulation modes 110, 120, namely, the parent vessel centerline, and the separated aneurysm. All analysis, measurements, and the virtual stent placement are driven by these two components, and their accuracy defines the overall accuracy of the method 100. For example, a virtual stent is deformed by the centerline and, aneurysm measurements are made on the separated aneurysm. To enhance the accuracy of these two components, three seed points are also used as reference input—the proximal and distal planes/points, $P_p$ and $P_d$, on either side of an aneurysm and a dome point $P_D$ to highlight the relative positioning of the aneurysm with respect to the proximal and distal points. The proximal and distal points $P_p$, $P_d$ determine the extent of the parent vessel that a user is interested in analyzing, and the extent of the virtual stent that will cover the parent vessel in between the two planes. FIG. 4 shows an example of the three seed points on a parent vessel. The use of these seed points assist in increasing the reliability and repeatability of the method 100 with minimal user input.

The input to the method 100 may be based, for example, on 3D digital subtraction angiographic (DSA) images due to the high contrast between the parent vessel and the background. The output of the method 100 is the aneurysm measurement report, the aneurysm geometry, and the deformed virtual stent. Also, the input to the simulation mode 120 is fed from the output of the preceding analysis mode 110 so that, advantageously, the method 100 is simple and intuitive for users.

The first step of the aneurysm analysis mode 110 is the user's selection of a 3D volume image of the patient (Step 131). The user specifically selects the volume image from the patient data accessed through the system 10. This may be done, for example, via a patient browser application that loads input data for the method 100. Also, the corresponding volume image may be displayed in three orthogonal multiplanar rendering (MPR) views and well as a volume rendering technique (VRT) display, each being a different visualization filter of the same data set. The user can select the entire volume image or restrict the analysis to a volume of interest (VOI) that includes the aneurysm, the parent vessel and surrounding vessels. Once the VOI is selected, the method 100 crops the 3D volume and performs an automatic vessel segmentation based on a predefined threshold parameter (Step 133). The surface of the vessel may be reconstructed after the vessel is extracted (Step 141).

Figure 5:
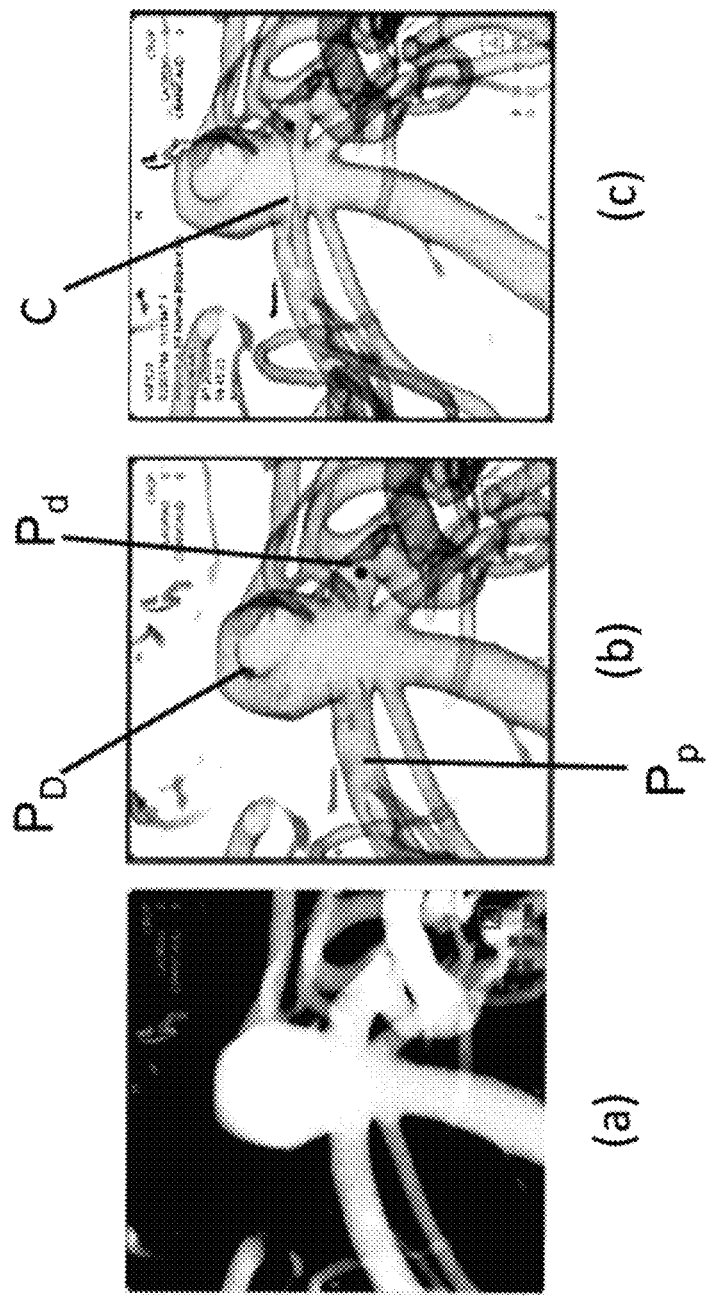
FIGS. 5a-5c are images of a segmented blood vessel of interest.

Once the segmentation is complete, the user defines the parent vessel segment or region of interest (ROI) by selecting proximal and distal points $P_p$, $P_d$ on the parent vessel around the aneurysm and one extra point in the aneurysm dome $P_D$ (Step 135). These seed points can be moved until the user is satisfied with the selection. The proximal and distal points are then used as seed points to extract the centerline of the selected parent vessel. The seed points are first centered in the parent vessel (Step 137) and the extracted centerline is computed (Step 139) and modeled as B-splines to describe the healthy vessel anatomy. The method 100 may use an algorithm for centerline extraction that combines two distance transforms to generate a skeleton of the healthy parent vessel. The first transform encapsulates the distance between the proximal point $P_p$ to every voxel inside the given region of interest while the second one encodes the distance from every voxel to the vessel boundary. Using these transforms, the algorithm finds the shortest path between the two given proximal and distal points while remaining as close to the vessel center as possible. The algorithm then applies a Gaussian filter to generate a smoother skeleton. Note, as described in later steps, to obtain a centerline of the healthy parent vessel, points close to the aneurysm are ignored as the extracted centerline could be deformed by the aneurysm geometry. FIGS. 5a-5c show an example of a segmented VOI (FIG. 5a), the three points selected by a user and defining the vessel segment of interest, $P_p$, $P_d$, $P_D$ (FIG. 5b), and the corresponding extracted vessel centerline C (FIG. 5c). Note that the generation of the vessel surface (Step 141) does not require centerline information, and may be done before, after, or in parallel to the centerline extraction steps, depending upon the process flow desired.

Figure 6:
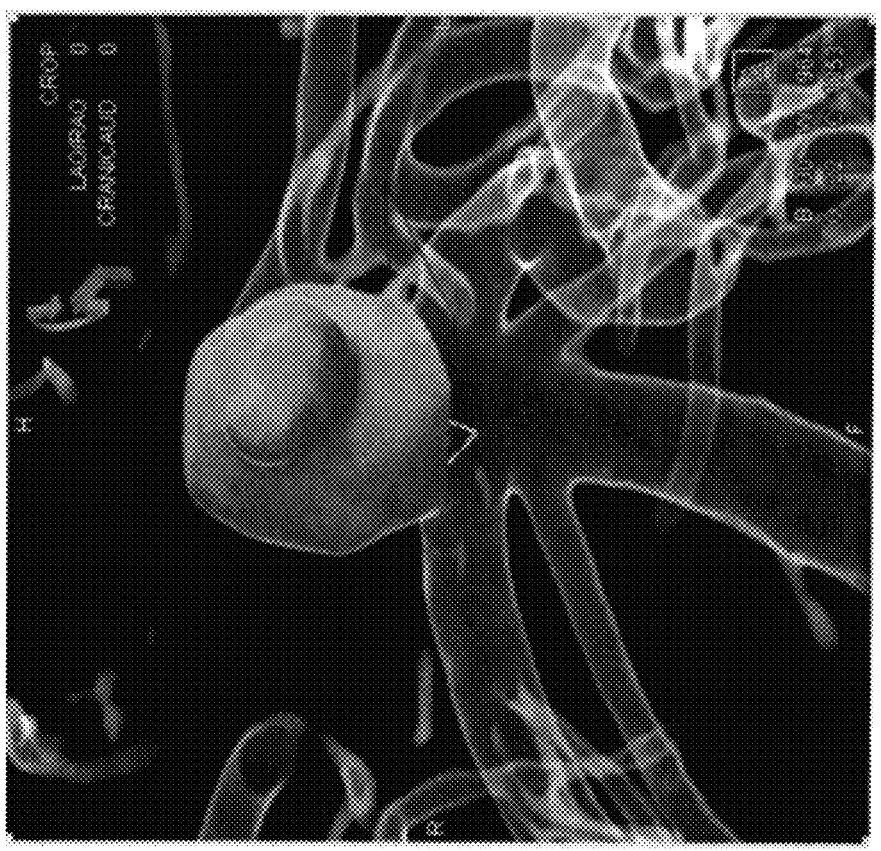
FIG. 6 is an image of a separated aneurysm.

After the centerline is extracted, the method 100 performs aneurysm separation (Step 143) and quantification. The method 100 may use an aneurysm separation algorithm that is based on strong priors (i.e., prior probability distributions) determined from the proximal, distal and dome points $P_p$, $P_d$, $P_D$. For the vessel prior, the shortest geodesic path from the proximal point $P_p$ to the distal point $P_d$ (mapped to the vessel surface) is used. The aneurysm prior is determined from the intersection between the vessel surface and a plane centered on the dome point $P_D$. The plane normal is directed from the closest point on the centerline to the dome point $P_D$. Once the seed points are determined, a graphcut based algorithm may be used in which the strong priors are combined to favor heavily towards their respective labels in the unary potential term. The pairwise potentials are determined from the average of the Gaussian curvature computed at the two neighboring vertices. The aneurysm boundary relates to points of the Gaussian curvature. FIG. 6 illustrates an exemplary result for the aneurysm separation. Aneurysm separation is discussed further in a paper by Sajjad Baloch, Erkang Cheng, Ying Zhu, Ashraf Mohamed, Haibin Ling, and Tong Fang, entitled "Shape based conditional random fields for the segmentation of intracranial aneurysms", MeshMed workshop on Mesh Processing in Medical Image Analysis in conjunction with MICCAI, 2011, pp 1-12, which is incorporated by reference herein.

Once the aneurysm is separated, the method 100 reconstructs a healthy parent vessel without the aneurysm (Step 145). A curved tube model is used to describe the shape of the healthy parent vessel, using the extracted vessel centerline and vessel diameters along the vessel. Generally, a set of planes perpendicular to the vessel centerline are generated and information about the parent vessel cross section such as the area and the minimum and maximum diameters is computed for each plane.

To prevent the vessel centerline from being affected by the bulging aneurysm, a refinement step may be carried out to obtain a more accurate or corrected vessel centerline at the place of aneurysm growth. First, the aneurysm ostium is projected onto the extracted centerline to determine and discard a stretch of the centerline potentially affected by the aneurysm. Then this segment of the centerline is replaced by smoothly reconstructing from the remaining parts of the centerline using B-spline interpolation. The refined centerline better models the healthy parent vessel independent of the aneurysm growth.

The method 100 then computes certain aneurysm measurements (i.e., aneurysm quantification) including the dome height and width, the ostium length, and the neck angle (Step 147). The method 100 may utilize measurement algorithms that consider two types of measurements on the aneurysms: VRT measurements and MPR measurements. VRT measurements are made on the 3D aneurysm, and include aneurysm volume and surface area, dome width, dome height, neck length and width. The method 100 may use a volume computation algorithm that is based on numerical integration, and involves adaptive discretization of the space enclosed by the aneurysm into rectangular bar elements. The volume of the individual bars is finally accumulated to compute the total volume. Surface area is computed as the sum of areas of all surface triangles and the neck length and width computation is carried out via PCA (i.e., principal component analysis). Dome width computation involves creation of an aneurysm profile by intersecting the aneurysm with a plane parallel to the ostium plane, which is shifted gradually to cover the entire range of the aneurysm. Once the profile is available, the width of each profile curve is computed through PCA, and the overall maximum is used as the dome width.

MPR measurements are made on the MPR slice perpendicular to the centerline. These measurements include neck angle, and maximum and mean diameters, and stent diameters. Neck angle is computed by first finding the intersection between the aneurysm boundary and the MPR plane. The angle formed by the two intersection points, and the vertex on the corresponding centerline point defines the neck angle. Maximum and mean diameters are computed based on the MPR contour obtained from the intersection between the MPR plane and the parent vessel. Distances between each pair of opposite points on the MPR contour are used to define diameters.

Figure 7:
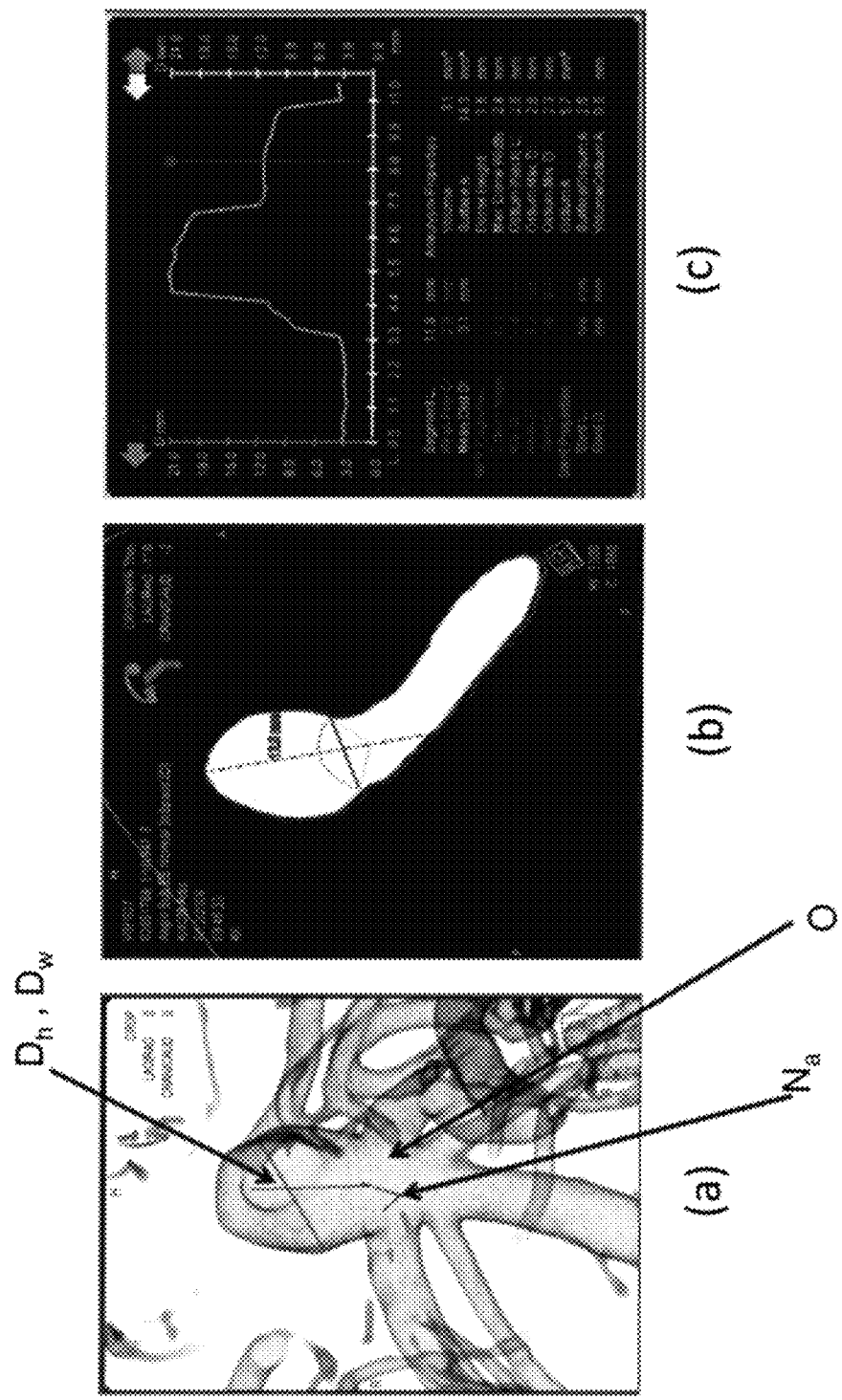
FIGS. 7a-7c are images of aneurysm measurement displays.
Figure 8:
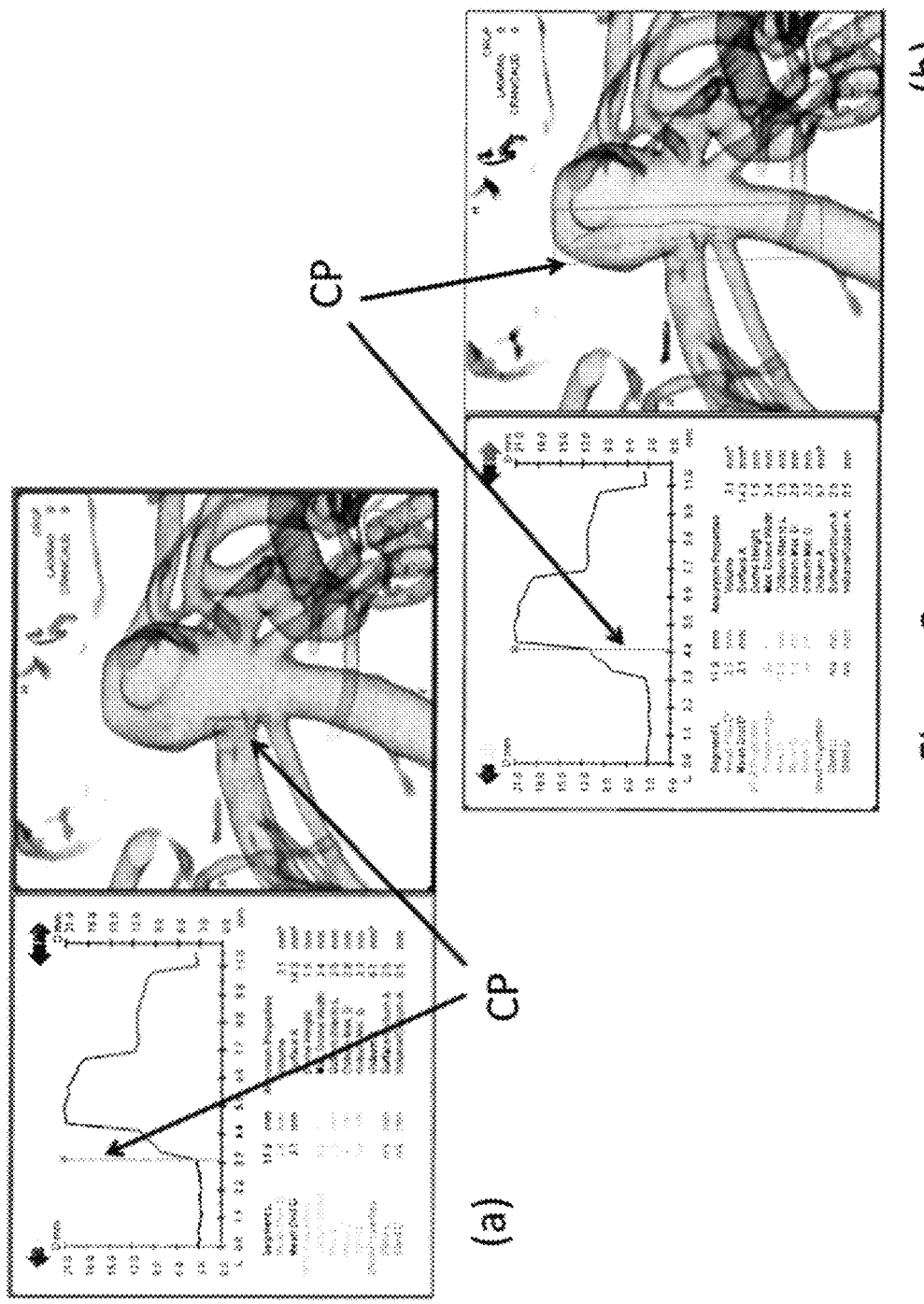
FIGS. 8a-8b are images of a clipping plane in a user interface that defines a parent vessel cross-section.

These measurements may be displayed by the method 100 for analysis by a user (Step 149), for example, on the VRT (shown in FIG. 7a) as well as in the MPR views (shown in FIG. 7b). The MPR view corresponds to the vessel cross section perpendicular to the parent vessel centerline. The ostium plane O, the dome height $D_h$ and the dome width $D_w$, and the neck angle $N_a$ are shown in FIG. 7a. In addition, a profile of the diameters may be displayed on a separate window (shown in FIG. 7c) together with the results of the aneurysm analysis together with MPR and VRT measurements. As part of the user interface, a user may move a clipping plane (MPR plane) CP that defines the parent vessel cross-section by dragging the plane in the VRT view or by moving the vertical line CP representing the clipping plane on the profile view (shown in FIGS. 8a and 8b). As the clipping plane CP moves along the centerline, the vessel cross-section on the MPR views and the corresponding MPR properties displayed in the profile view are updated.

Figure 9:
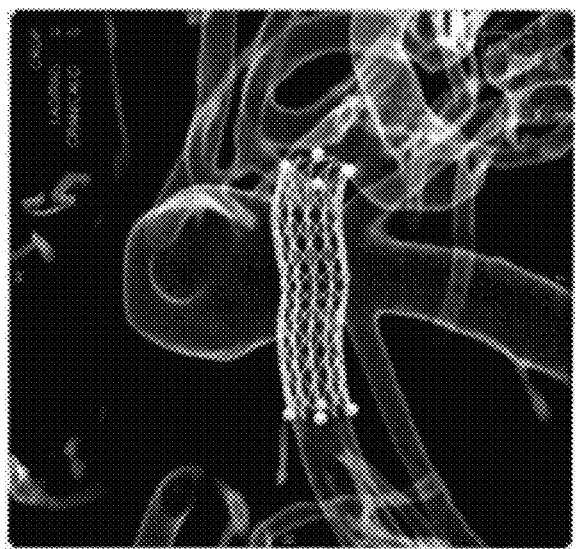
FIGS. 9a-9b are images of a virtual stent.
Figure 9:
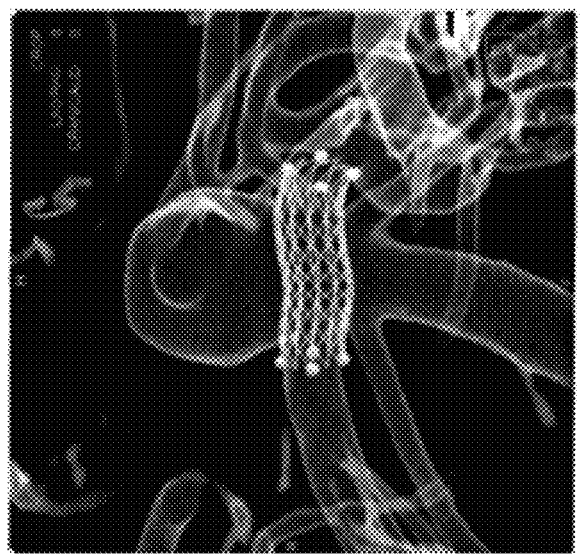

If the user is not satisfied with the results, a user may edit the control points of the B-spline that defines the centerline and repeat the separation and quantification analysis or may edit the boundary of the aneurysm separation result and repeat the quantification analysis only (Step 151). Otherwise, as noted above, the output of the aneurysm analysis mode 110 serves as the input for the stent simulation mode 120 of the method 100. The extracted centerline and results of the aneurysm analysis are used to automatically design and place a virtual stent on the parent vessel (Step 153). Generally, a 3D virtual stent is created, and bent using the centerline (i.e., the centerline defines the axial stent deformation). The virtual stent is expanded based on the vessel geometry while taking the healthy vessel diameter into account. This prevents the virtual stent from going inside the aneurysm area, while creating a vessel tight configuration. The user may adjust the stent configuration by modifying the stent length, the stent diameter, as well as its location (Step 155). FIGS. 9a and 9b illustrate a full length virtual stent and user-adjusted length to make the virtual stent smaller, respectively.

Figure 10:
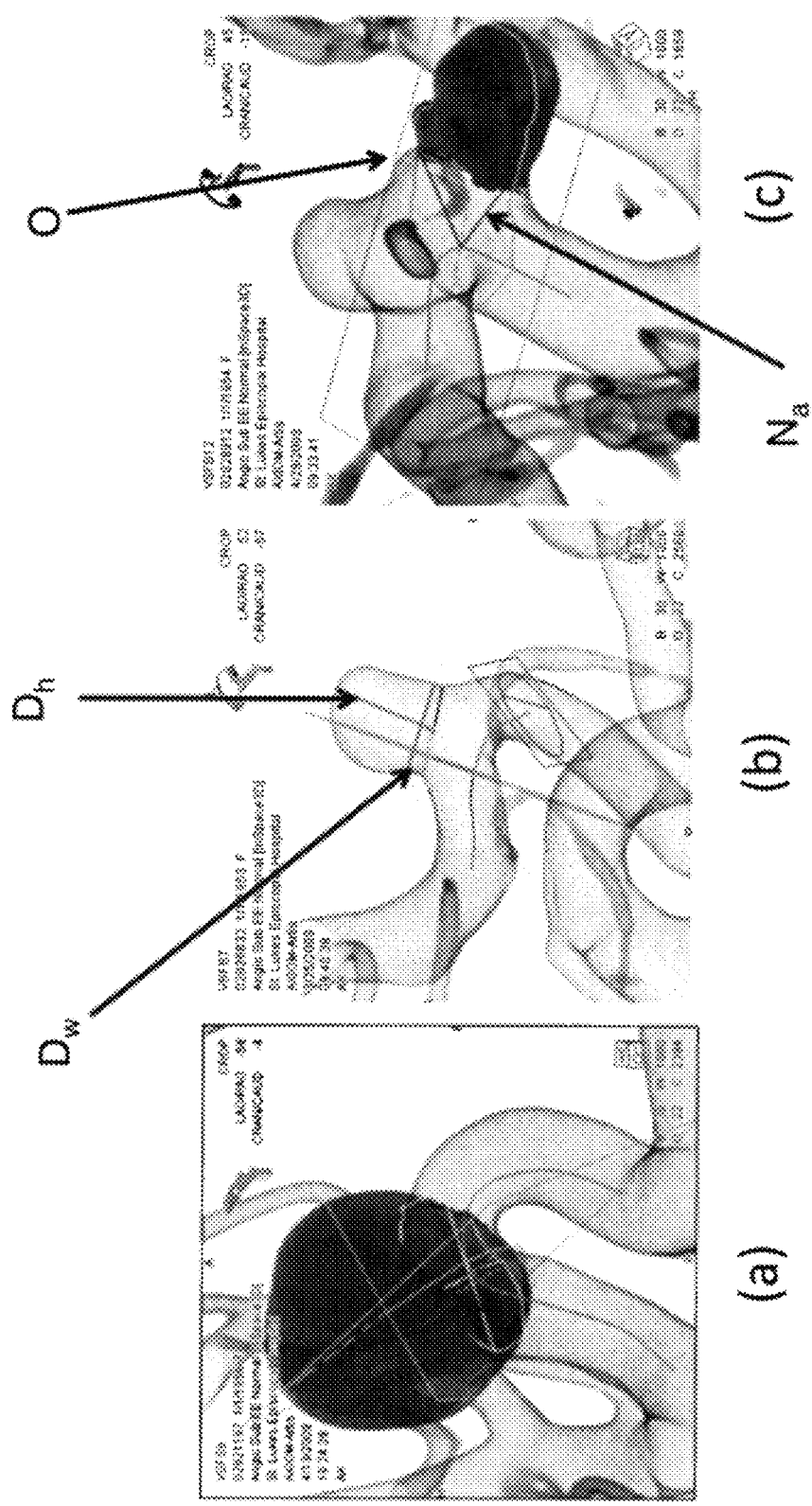
FIGS. 10a-10c are images of aneurysm measurements in VRT view.
Figure 11:
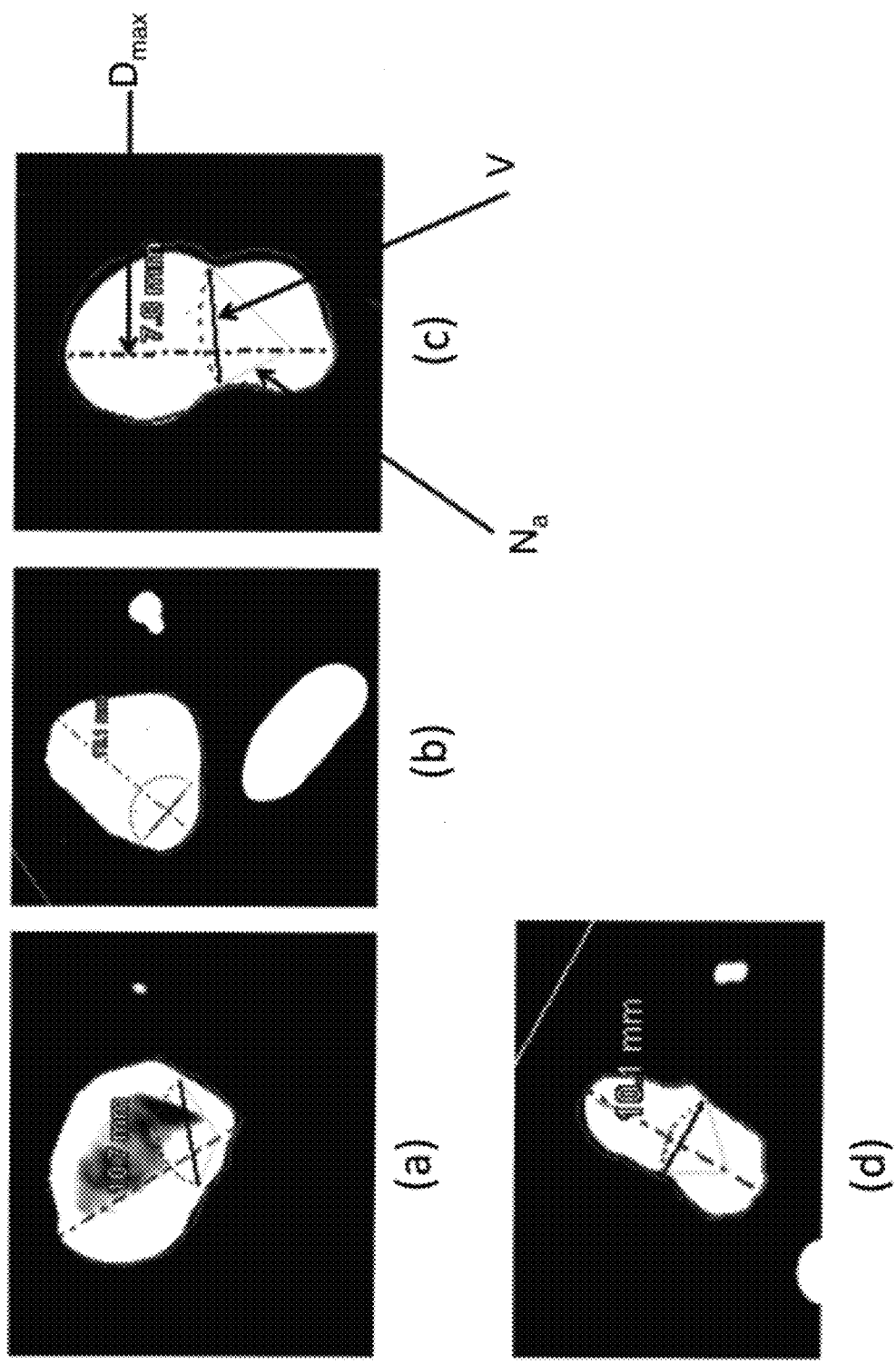
FIGS. 11a-11d are images of aneurysm measurements in MPR view.
Figure 12:
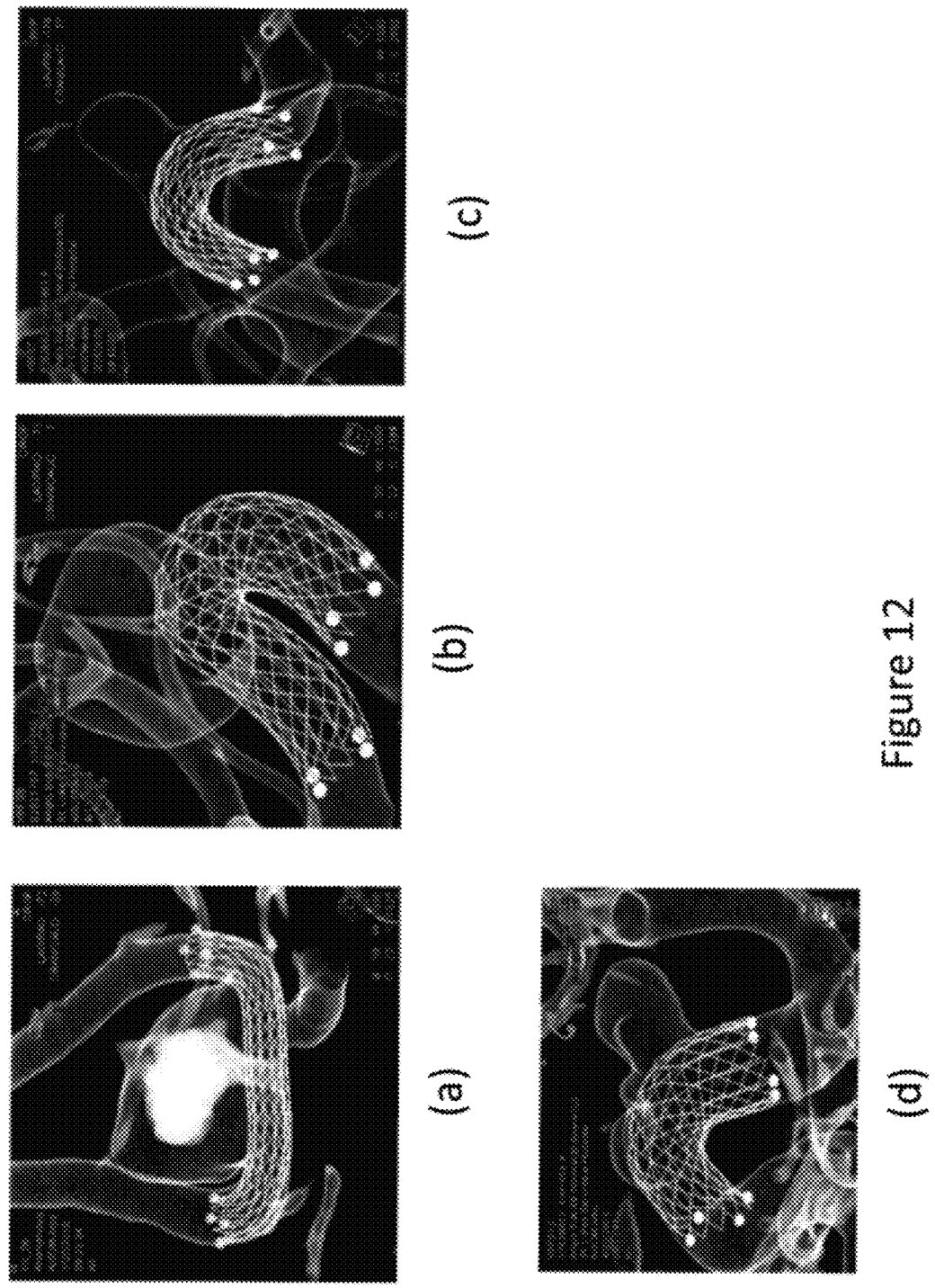
FIGS. 12a-12d are images of various virtual stents.

Experimental and testing results show that the method 100 provides a high degree of stability and repeatability of aneurysm measurements as well as speed and accuracy. For example, all the measurements were found to be very stable, with small perturbations (1/10th of the dome size) in the seed points. On average, it took about 20 seconds to run the aneurysm analysis mode, and stent design and placement was accomplished in a fraction of a second. FIGS. 10 through 12 present some results generated by the method 100. FIGS. 10a-10c show measurements results in the VRT view, in particular, an aneurysm separation is shown in FIG. 10a and dome width $D_w$ and dome height $D_h$ are shown in FIG. 10b. FIG. 10c shows the MPR plane, the ostium plane O which marks the boundary of the ostium, and the neck angle $N_a$ for the given MPR plane. FIGS. 11a-11d show measurements results in the MPR view, in particular, a reconstructed parent vessel V, the neck angle $N_a$, and the maximum diameter $D_{max}$ (indicated in FIG. 11c). FIGS. 12a-12d show stent placement for various cases. Note that the figures include vessels with varied level of complexity, containing bifurcations as well as high vessel curvature. The method 100 effectively computed different measurements and displayed them in various views.

Further, some of the method 100 results were compared to manual analysis and planning (i.e. a manual delineation of the boundaries of the aneurysm and subsequent computation of volume measurement) for a number of cases. On average, the method 100 was 88% in accordance with the manual analyses for the cases, which did not have major leaks in aneurysm separation. Out of 55 cases tested, 7 resulted in major to moderate leaks, mainly for cases which have touching vessels. For surface area, the method 100 results were consistent with those yielded by VTK (i.e., Visualization Toolkit software).

Advantageously, the method 100 of the present invention may assist physicians in accurately assessing intracranial aneurysms and efficiently planning for endovascular intervention. The method 100 provides computer-aided tools to measure and visualize various patient-specific geometric parameters of pathological vessels with better repeatability and accuracy. Based on patient-specific measurements, the method 100 also simulates the placement of virtual stents that conform to the shape of the diseased vessels, to better support clinical decisions on stenting and selection of device types. The method 100 is highly stable and is capable of handling complex cases.

Other modifications are possible within the scope of the invention. For example, the subject patient to be scanned may be a human subject, animal subject or any other suitable object. Also, although the steps of the method 100 or other methods have been described in a specific sequence, the order of the steps may be re-ordered in part or in whole and the steps may be modified, supplemented, or omitted as appropriate. Also, the method 100 or other methods may use various well known algorithms and software applications to implement the steps and substeps. Further, the method 100 or other methods may be implemented in a variety of algorithms and software applications. Further, the method 100 or other methods may be supplemented by additional steps or techniques. It is also understood that the method 100 or other methods may carry out all or any of the steps using real-time data, stored data from a data archive or database, data from a remote computer network, or a mix of data sources.

Also, the various described instrumentation and tools are conventional and well known. They may be configured and interconnected in various ways as necessary or as desired. Further, although in the described method 100 or other methods the user may use self-contained instrumentation and tools, the user may use other instrumentation or tools in combination with or in place of the instrumentation and tools described for any step or all the steps of the respective method, including those that may be made available via telecommunication means. Further, the described method 100 or other methods, or any respective steps, may be carried out automatically by appropriate instrumentation and tools or with some manual intervention.

What is claimed is:

1. A computer-assisted method of analyzing an intracranial aneurysm and virtually configuring endovascular treatment for the aneurysm, said method being carried out by a processor associated with an a medical imaging system to carry out the steps of the method, wherein the medical imaging system includes a medical imaging scanner that acquires image data and is operably connected to a computer system that controls operation of the scanner and, via a communication channel, to an image processing system that processes the image data signals and that has an image data archive or database adapted to store the image data signals that are produced by the image scanner, an application server, and a user workstation, the method comprising the steps of:
   a. receiving, by the processor, a user selected 3D digital subtraction angiographic (DSA) image that includes a parent blood vessel with an aneurysm;
   b. performing vessel segmentation by the processor on the selected 3D DSA image and outputting a segmented digital image of the parent blood vessel;
   c. receiving, by the processor, a proximal point in the parent vessel around the aneurysm selected by a user from the segmented digital image, a distal point in the parent vessel around the aneurysm selected by a user from the segmented digital image, and a point in a dome of the aneurysm selected by a user from the segmented digital image;
   d. centering, by the processor, the proximal and distal points in the parent vessel in the segmented digital image;
   e. extracting, by the processor, the centerline of the parent blood vessel from the segmented digital image using the centered proximal and distal points as seed points wherein the centerline is identified in the parent blood vessel in the segmented digital image;
   f. separating, by the processor, the aneurysm from the parent blood vessel, based on the proximal point, distal point, and point in the dome, wherein the separated aneurysm is identified in the segmented digital image as separate from the parent blood vessel;
   g. reconstructing, by the processor, a healthy parent blood vessel in the segmented digital image after separating the aneurysm from the parent blood vessel;
   h. displaying to the user a plurality of characteristic features of the aneurysm calculated after the aneurysm was separated from the healthy parent blood vessel; and
   i. configuring, by the processor, a 3D virtual stent in the segmented digital image from the extracted centerline of the parent blood vessel and the plurality of characteristic features that fits the reconstructed parent blood vessel.

2. The method of claim 1, wherein the performing step comprises reconstructing a surface representation of the parent blood vessel in the segmented digital image.

3. The method of claim of claim 1, further comprising generating in the segmented digital image a skeleton of the parent blood vessel without the aneurysm.

4. The method of claim 1, wherein the separating step is implemented using proximal and distal points on the parent blood vessel around the aneurysm and one point in the aneurysm dome.

5. The method of claim 1, wherein the reconstructing step comprises reconstructing the parent blood vessel in the segmented digital image with the aneurysm separated from the parent blood vessel using the extracted centerline and computed diameters along a length of the parent blood vessel.

6. The method of claim 5, wherein the reconstructing step comprises reconstructing the extracted centerline without points projected thereon from the aneurysm.

7. The method of claim 6, wherein reconstructing the extracted centerline comprises reconstructing the extracted centerline from an interpolation of points of the extracted centerline without points projected thereon from the aneurysm.

8. The method of claim 1, wherein the plurality of characteristic features comprise aneurysm volume and surface area, dome width, dome height, neck length and width, neck angle, and maximum and mean diameters.

9. The method of claim 1, wherein the configuring step comprises designing and placing the virtual stent on the parent blood vessel in the segmented digital image.

10. The method of claim 1, wherein the extracted centerline defines axial stent deformation.

11. The method of claim 1, wherein step c further comprises adjusting the proximal, distal and dome points.

12. The method of claim 1, further comprising, after displaying to the user the plurality of characteristic features of the aneurysm, receiving user edits of control points of the centerline.

13. The method of claim 1, further comprising, receiving, from the user, adjustments to the 3D virtual stent configuration.

14. The method of claim 13, wherein adjustments to the 3D virtual stent configuration include modifications of stent length, stent diameter, and stent location.

* * * * *